United States Patent [19]

Adair

[11] 4,250,882
[45] Feb. 17, 1981

[54] WOUND DRAINAGE DEVICE

[75] Inventor: Edwin L. Adair, Littleton, Colo.

[73] Assignee: Medical Dynamics, Inc., Englewood, Colo.

[21] Appl. No.: 6,784

[22] Filed: Jan. 26, 1979

[51] Int. Cl.³ .......................... A61F 5/44; A61F 13/00
[52] U.S. Cl. .................................... 128/275; 128/154; 128/350 R; 128/297
[58] Field of Search ................ 128/350 R, 297, 298, 128/303 R, 154, 132 R, 275, 276, 283

[56] References Cited

U.S. PATENT DOCUMENTS

| | | | |
|---|---|---|---|
| 2,305,289 | 12/1942 | Coburg | 128/132 R |
| 2,441,508 | 5/1948 | Porcell | 128/283 |
| 2,524,750 | 10/1950 | Bellinger | 128/283 |
| 2,869,548 | 1/1959 | Mason | 128/283 |
| 3,483,868 | 12/1969 | Marsan et al. | 128/283 |
| 3,865,109 | 2/1975 | Elmore | 128/275 |
| 3,954,105 | 5/1976 | Nordby et al. | 128/283 |
| 4,159,720 | 7/1979 | Burton | 128/260 |

Primary Examiner—Robert W. Michell
Assistant Examiner—J. L. Krutor
Attorney, Agent, or Firm—Sheridan, Ross, Fields & McIntosh

[57] ABSTRACT

A drainage device for attachment to a portion of the skin of an individual is provided. The device comprises a flange which sealingly engages the skin and has an opening therein to overlie a wound in the skin tissue. A ring member having a channel formed therein is mounted on a side of the flange opposite that side of the flange engaging the skin. A locking clip is connected to the ring member and extends laterally between portions thereof. A drainage strip is releasably held in the locking clip and inserted into the wound so that drainage of the wound occurs. A removable cover member grippingly engages the outer wall of the ring member to prevent the drainage from escaping the confines of the device.

24 Claims, 11 Drawing Figures

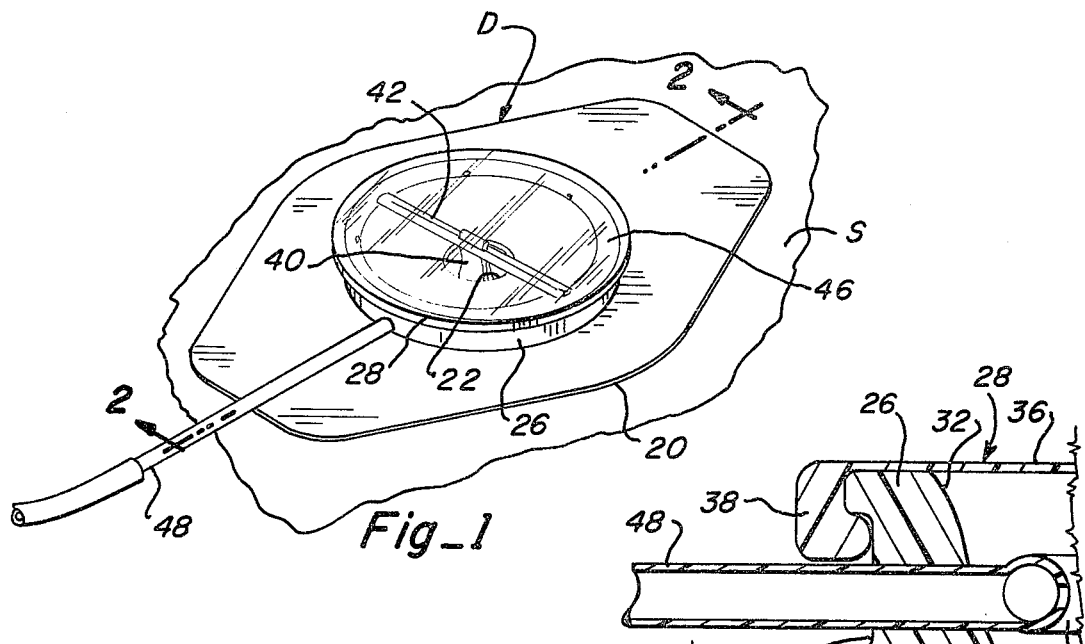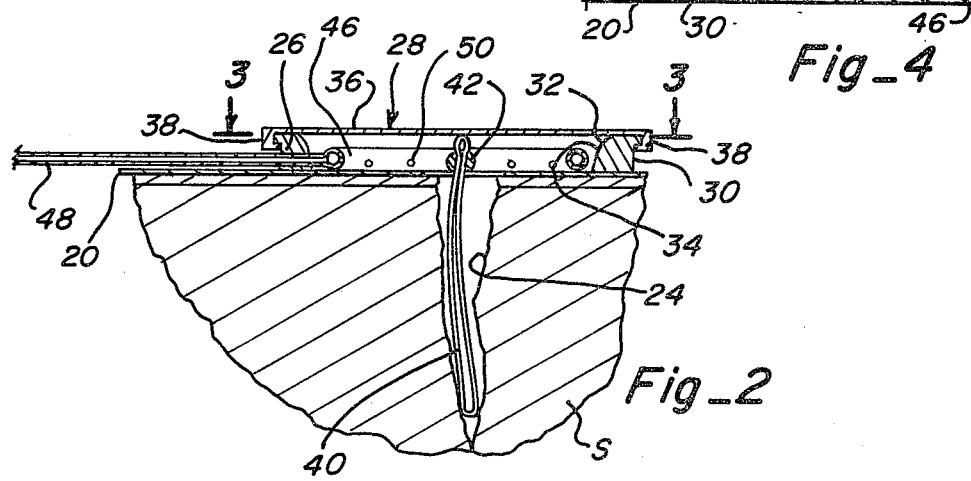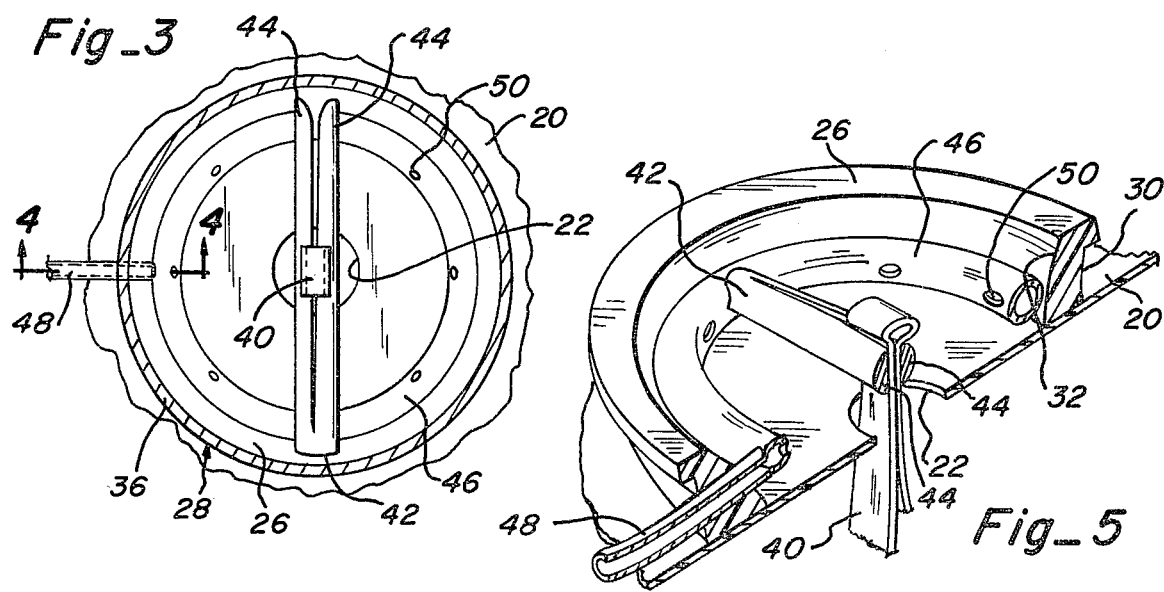

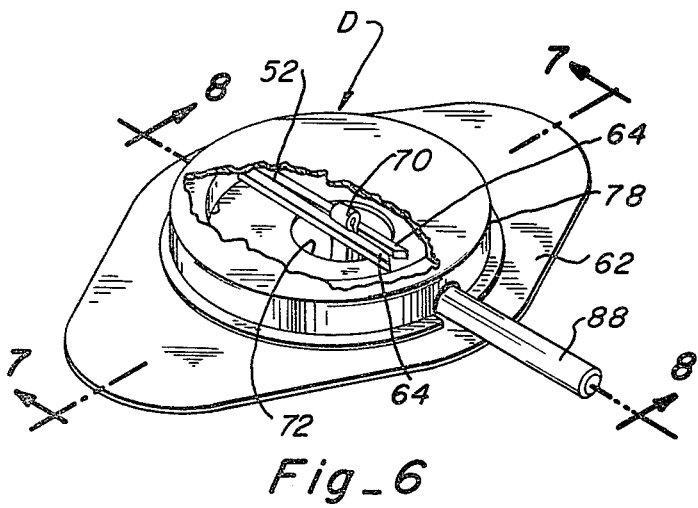
Fig_6
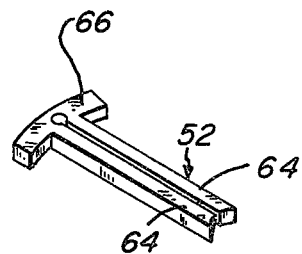
Fig_11
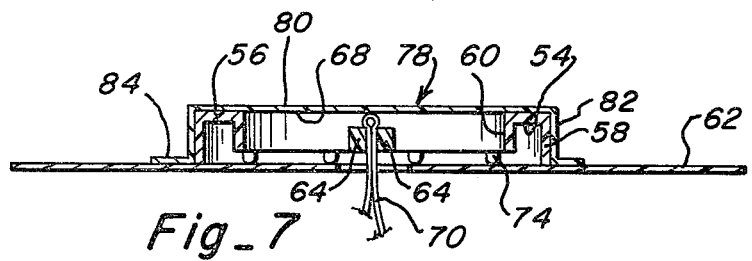
Fig_7
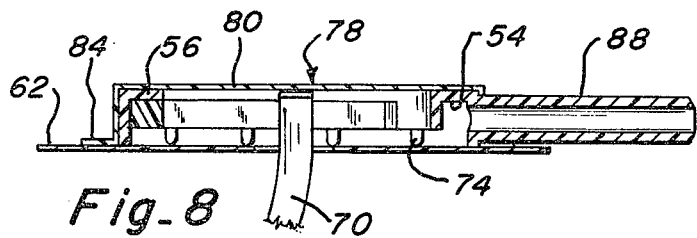
Fig_8
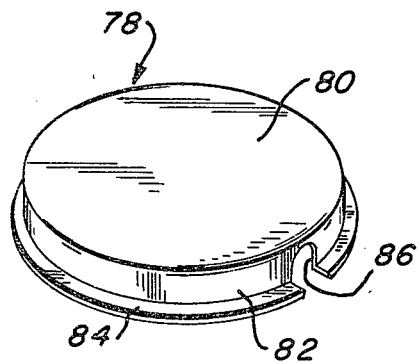
Fig_9
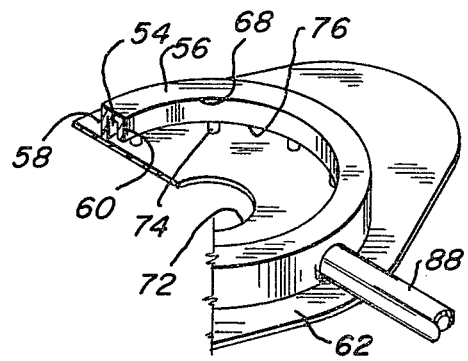
Fig_10

WOUND DRAINAGE DEVICE

DESCRIPTION

1. Technical Field

This invention relates to devices which are placed in contact with the skin tissue of a patient while overlying an opening in the skin to facilitate the draining thereof, and in particular to a device which sealingly engages the skin tissue and overlies a wound therein to aid in the drainage of the wound while permitting observation and treatment of the wound without the necessity of completely removing the device from the skin.

2. Background Art

A number of drainage devices have been developed to enable and facilitate the draining of fluid from a wound or a cut formed in the skin tissue of an individual. In U.S. Pat. No. 3,026,874 to Stevens, a wound shield is shown having a strap for connecting the shield to the patient. U.S. Pat. No. 3,954,105 to Nordby, et al. shows a gelatinous material engaging the skin of an individual. The material may be provided with an orifice through which a tubular drain is inserted into a wound or opening in the skin. In addition to the wound drainage devices, U.S. Pat. No. 3,618,606 to Brown, et al. discloses a stoma bag having a flange which directly contacts the skin area surrounding an opening and thereby sealingly engages the skin to prevent material discharged from the opening from escaping the stoma bag.

The wound drainage device described herein, on the other hand, includes a locking element traversing an opening in the skin tissue for removably holding a drainage strip which is inserted into the skin opening. This locking element facilitates the removal and replacement of the drainage strip from the skin opening. Since the drainage strip is incrementally withdrawn on a regular basis as healing progresses, it is necessary that easy access and removal of such strips be provided.

DISCLOSURE OF INVENTION

In accordance with the present invention, a drainage device is provided which includes a flange adaptable to engage the skin of a patient and which has an aperture to be positioned over an opening in the skin tissue. A base section having a large orifice centrally formed therein is connected to a side of the flange opposite that side which engages the skin. The drainage device further comprises a locking member fastened to the base section and extending between portions thereof to releasably grip a drainage strip which is inserted into the skin opening. A removable lid overlies the base section orifice to prevent escape of fluid or other material entering the device.

More particularly, the drainage device comprises a flat, thin flange which directly contacts and is adaptable to sealingly engage the outer skin tissue of the patient. An aperture is centrally formed in the flange and is of a dimension so that it completely exposes an opening in the skin tissue. An annulus member is centrally positioned and connected to a side of the flange opposite that side which engages the patient's skin. The annulus includes an opening in which an outlet tube is held.

The drainage device further includes a locking member having a pair of spreadable, resilient wings between which a drainage strip is releasably held. The locking member is connected at one end to the annulus member and extends laterally between portions of an inner wall of the annulus member. The drainage strip is positioned in the locking member so that it is easily insertable through the flange aperture into the skin opening. A removable cap member covers the area within the inner wall of the annulus member so that the fluid or other material entering the device cannot escape through that defined area. The cap member includes a cover portion which contacts a surface of the annulus opposite that surface which connects with the flange. A ring portion is connected to the outer edge of the cap cover portion and extends generally perpendicularly therefrom. The ring portion of the cap member is contiguous with an outer wall of the annulus member to grippingly secure the cap member thereto. An opening is formed in the ring portion so that the outlet tube held in the annulus is receivable therethrough. The outlet tube is capable of either removing fluid drained from the opening in the skin tissue or delivering medication or other necessary material to the skin opening.

Accordingly, a drainage device having a clip element for releasably holding a drainage strip is provided. It can be appreciated that the cap member is easily removed from the annulus member to permit access to the drainage strip and the opening or wound in the skin tissue. The replacement of the clip-held drainage strip is facilitated while the drainage device remains securely attached to the skin tissue during the replacement. Additional advantages of this invention will be readily apparent from the description which follows taken in conjunction with the accompanying drawings.

BRIEF DESCRIPTION OF THE DRAWINGS

FIG. 1 is a perspective view of the drainage device attached to the skin and overlying an opening in the skin tissue;

FIG. 2 is a longitudinal section, taken along line 2—2 of FIG. 1, showing a drainage strip connected to the device and inserted into the skin opening;

FIG. 3 is a top plan view, taken along line 3—3 of FIG. 2, showing details of the drainage device with a portion of the cap cut away;

FIG. 4 is an enlarged fragmentary longitudinal section, taken along line 4—4 of FIG. 3, showing details of the tube for carrying fluid drained from the skin opening or delivered thereto;

FIG. 5 is an enlarged fragmentary perspective view of the drainage device showing further details of the locking member, drainage strip, and the outlet tube;

FIG. 6 is a perspective view of another embodiment of the drainage device;

FIG. 7 is a longitudinal section, taken along line 7—7 of FIG. 6, showing details of the drainage strip held by the locking member;

FIG. 8 is a longitudinal section, taken along line 8—8 of FIG. 6, showing further details of the tube for carrying material from and into the skin opening;

FIG. 9 is a perspective view of the cap as shown in the embodiment of FIG. 6;

FIG. 10 is a fragmentary perspective view of the drainage device showing details of the annulus without the locking member connected thereto; and FIG. 11 is a perspective view of the locking member of the embodiment of FIG. 6.

BEST MODE FOR CARRYING OUT THE INVENTION

In accordance with this invention, a wound drainage device D is provided having a flange 20 adaptable to sealingly engage the skin S of a patient, as seen in FIG. 1. Flange 20 is a thin, relatively flat resinous member which is fixedly secured to the skin S after applying any number of conventional adhesive substances to a first side of flange 20 which then contacts and adheres to the skin S. Flange 20 is depicted in FIG. 1 as a generally six-sided polygon, although other shapes may be utilized. An aperture or inlet 22 is centrally formed in flange 20 to overlie and completely expose an opening or wound 24 in the skin S. Extending generally perpendicularly to the plane of flange 20 is a base member or collar 26 which is shown in FIG. 2 as being generally in the form of an annulus. A cap member or lid 28, preferably transparent, overlies base member 26 to contain material received within the device D.

As seen in FIG. 2, base member 26 includes an outer or first wall 30 and an inner or second wall 32 which has a circumferential dimension less than outer wall 30. A space 34 is defined by the area bounded by inner wall 32. The surface of a first side of base member 26, defined by the area between outer wall 30 and inner wall 32, is sealingly connected to a second side of flange 20. Second side of flange 20 is opposite the first side thereof which is secured to the skin S.

FIG. 2 also shows, as does FIG. 4, the cap member 28 having a cover portion 36 and a lip portion 38, which is generally L-shaped in cross-section. Cover portion 36 of cap member 28 traverses space 34 and contacts the area between outer wall 30 and inner wall 32 while lip portion 38 grippingly engages outer wall 30 of base member 26 to secure the cap member 28 thereon.

A drainage strip 40 is supported by a locking member or clip 42. Drainage strip 40 is inserted through the flange aperture 22 and into the skin opening 24. Strip 40 is sterilized and of sufficient length to be inserted into wound 24 to permit the drainage of fluid therefrom prior to allowing the continuation of the healing process. As best seen in FIG. 3, locking member 42 includes a pair of wings 44 connected at their first ends while their second ends are parallel spaced from each other. Wings 44 are elongated, resilient members such that the space between them may be forcibly increased to insert drainage strip 40 therebetween. Upon releasing the wing separating force, the second ends of wings 44 return to a position which securely holds drainage strip 40. Locking member 42 extends laterally between portions of inner wall 32 while the drainage strip 40 is supported adjacent the longitudinal center of the locking member 42 so that it is axially aligned with the skin opening 24. Also seen in FIG. 3 is a tubular receiving member 46 which is positioned inwardly adjacent inner wall 32 of base member 26.

As illustrated in FIGS. 2 and 4, an outlet tube 48 is inserted through a bore or opening formed between outer wall 30 and inner wall 32, and is of a dimension to fixedly hold outlet tube 48 therein. FIG. 4 also shows the L-shaped lip portion 38 of cap member 28 gripping the outer wall 30 to releasably secure cap member 28 to base member 26.

Operation of drainage device D is best illustrated in FIG. 5. Drainage strip 40, which is releasably fastened to locking member 42, is inserted into skin opening or wound 24 and provides a means for draining the fluid contained therein. Locking member 42 is connected to tubular receiving member 46 which has passages 50 into which the fluid moves as it escapes the skin opening 24 and the flange aperture 22. Outlet tube 48 which is connected to tubular receiving member 46 accepts the fluid as it moves through the tubular receiving member 46. The fluid is then removed by the outlet tube 48 into a receptacle (not shown). This movement of fluid may result either because of gravity when the device D is appropriately placed on the skin S or because of the drawing action of a suction apparatus (not shown).

FIG. 6 illustrates another embodiment of the drainage device D which utilizes a locking member 52, as shown in FIG. 11, and includes a channel 54 in annulus or collar 56, as seen in FIG. 7. This channel 54 is formed between the parallel spaced outer wall 58 and inner wall 60 of annulus 56. Outer wall 58 and inner wall 60 are positioned generally perpendicularly to flange 62.

The locking member 52 of FIG. 11 has a pair of parallel wings or prongs 64 which are separated from each other along their longitudinal axes while joined together by a cross member 66 perpendicularly connected at one end of the prongs 64. Similar to the embodiment previously described, the prongs 64 may be forcibly spread apart. The prongs 64 resiliently return to a parallel position upon release of the force. As depicted in FIG. 8, cross member 66 is of a dimension to be securely held in channel 54 between outer wall 58 and inner wall 60 while an opening is provided in inner wall 60 to permit entry of prongs 64 therethrough. Prongs 64 laterally extend from inner wall 60 for a portion of the distance across space 68 so that drainage strip 70 may be inserted through aperture or inlet 72 which is centrally formed in flange 62.

As illustrated in FIG. 7, inner wall 60 is of a vertical dimension less than outer wall 58 while a plurality of spaced projecting members or feet 74 are connected to inner wall 60 and extend adjacent to flange 62 thereby forming a series of passages 76 between the feet 74.

The cap member or lid 78 of FIG. 9 is provided with this embodiment and includes a cover portion 80 which overlies space 68 and is contiguous with the surface area between outer wall 58 and inner wall 60. A ring member 82 is connected to cover portion 80 along its circumferential edge and extends generally perpendicularly from cover portion 80. Ring member 82 grippingly engages outer wall 58 to secure cap member 78 to annulus 56 so that drainage material is unable to escape through space 68. Extending outwardly from an edge of ring member 82 is a rim 84 which contacts the side of the flange 62 opposite that side which is adaptable to sealingly engage the skin S. A hole 86 is provided in rim 84 and ring member 82 to permit entry of an outlet tube 88 fixedly positioned in an opening formed in outer wall 58 as shown in FIG. 8.

In using the embodiment of FIG. 6, fluid drained from a skin opening is received through the aperture 72 and flows between the feet 74 through passages 76 into channel 54. The drainage material moves through the channel 54 until it reaches outlet tube 88 which then removes the material from the drainage device D by means of gravity or a suction apparatus (not shown) connected to the outlet tube 88. As seen in FIG. 10, inner wall 60 is not connected to flange 62 so that the drainage material flows between the feet 74 which are adjacent the inner wall 60. But outer wall 58 sealingly engages flange 62 so that the drainage remains in the channel 54 and is unable to escape the drainage device D except through outlet tube 88.

From the foregoing, the advantages of this invention are readily apparent. A drainage device has been provided which is of relatively simple construction, yet very efficient in operation. A flexible locking clip securely holds a drainage strip and is positioned to facilitate the replacement thereof. In addition, a transparent lid engages the outer wall of the collar to contain any drainage fluid while permitting easy access to inspect the wound and remove the drainage strip.

The invention has been described in detail with particular reference to a plurality of embodiments thereof, but it will be understood that variations and modifications can be effected within the spirit and scope of the invention.

I claim:

1. A drainage device for attachment to the skin of a patient while overlying an opening in the skin tissue and adapted for use with a drainage strip which is insertable into the opening to permit drainage thereof, said device comprising:
    a flange including a first side for sealingly engaging the skin and a second side opposite first side, said flange having an inlet therethrough for overlying the opening in the skin tissue to permit entry of drainage material from the skin opening;
    collar means connected to said second side of said flange and having an opening to discharge the drainage material containable within said collar means; and
    a locking member connected to said collar means, said locking member including a pair of resilient wings connected together at their first ends and spreadable from each other at their second ends.

2. The device, as claimed in claim 1, further including:
    a cap member removably held on said collar means to contain drainage material therein while permitting access to the drainage strip.

3. The device, as claimed in claim 1, further including:
    means connected to said opening of said collar means for receiving the drainage entering said flange inlet.

4. The device, as claimed in claim 3, wherein said drainage receiving means includes:
    a tube receiving member contained within the said collar means having a plurality of passages formed therein to receive the drainage material from the skin opening; and
    an outlet tube connected to said tube receiving member and held in said collar opening for carrying the drainage material from said collar means.

5. The device, as claimed in claim 1, wherein:
    said locking member is elongated and extends laterally for a part of the distance between different portions of said collar means.

6. The device, as claimed in claim 1, wherein:
    said collar means is an annulus having a first wall and a second wall and in which said first wall has a greater circumferential dimension than said second wall.

7. The device, as claimed in claim 6, wherein:
    said annulus includes a channel generally perpendicular to said flange and formed between said first wall and said second wall.

8. The device, as claimed in claim 1, wherein:
    said collar means includes a first wall and a second wall in which the vertical dimension of said first wall is greater than said second wall so that drainage material passes below said second wall.

9. The device, as claimed in claim 8, including:
    a plurality of spaced projecting members connected to an edge of said second wall and extending adjacent to said flange thereby defining a plurality of passages between said projecting members to permit entry of the drainage material.

10. A drainage device for directly contacting a portion of the skin of a patient while overlying an opening in the skin tissue and adapted for use with a drainage strip to permit proper drainage of the skin opening, said device comprising:
    a flange including a first side for sealingly engaging the skin of a patient and a second side opposite said first side, said flange having an aperture in said first side which completely exposes the opening in the skin tissue to receive the drainage therefrom;
    a collar sealingly connected to said second side of said flange and including a first wall and a second wall with a channel formed therebetween, said channel formed generally perpendicular to said flange to receive the drainage material, wherein said collar is an annulus in which said first wall has a greater circumferential dimension than said second wall; and
    a locking member connected to said collar.

11. The device, as claimed in claim 10, wherein:
    said first wall of said collar is of a greater vertical dimension than said second wall of said collar so that drainage material passes below said second wall.

12. The device, as claimed in claim 11, wherein:
    said collar further includes a plurality of spaced projecting members connected to said second wall to define a number of passages therebetween through which the drainage flows into said channel.

13. The device, as claimed in claim 10, further including:
    a cap member having a generally circular cover portion and a ring member generally perpendicular to said cover portion and connected to the circumferential edge of said cover portion, wherein said ring member grippingly engages a portion of said first wall of said collar to contain the drainage received by said channel of said collar from the skin opening.

14. The device, as claimed in claim 10, wherein:
    said locking member includes a pair of spreadable resilient wings connected to said collar for receiving the drainage strip therebetween.

15. The device, as claimed in claim 14, wherein:
    said locking member further includes a cross member connected to first ends of said wings and held in said channel to support said wings within said collar.

16. The device, as claimed in claim 10, including:
    an outlet tube connected to said first wall of said collar to carry the drainage received from the skin opening.

17. A drainage device for attachment to the skin of a patient to permit drainage of a wound in the skin, said device comprising:
    a flange including a first side for sealingly engaging the skin and a second side opposite said first side, said flange having an aperture centrally formed therein for overlying and completely exposing the wound;

an annulus including:

a first wall having an opening and sealingly connected to said second side of said flange to prevent the escape of drainage therethrough, a second wall having an opening and connected to said first wall to define a channel therebetween, and a plurality of spaced feet connected to and projecting from said second wall to said second side of said flange thereby forming a plurality of passages between said feet to permit the movement of drainage into said channel;

a locking member having a cross member securely held within said channel and a pair of resilient wings connected at their first ends to said cross member and inserted through said second wall opening, wherein said wings extend laterally for a part of the distance between different portions of said second wall to overlie said flange aperture;

a drainage strip supported between said wings and in a position to be inserted into the wound;

a lid having a cover portion which overlies said annulus and a ring portion connected to the circumferential edge of said cover portion, wherein said ring portion grippingly engages said first wall of said annulus to prevent escape of the drainage contained within said annulus; and an outlet tube held in said first wall opening to permit the escape of the drainage as it moves along said channel.

18. A drainage device for attachment to the skin of a patient while overlying an opening in the skin tissue and adapted for holding a drainage strip which is insertable into the opening to permit drainage thereof, said device comprising;

a flange including a first side for sealingly engaging the skin and a second side opposite said first side, said flange having an inlet therethrough to overlie the opening in the skin tissue to permit entry of drainage material from the skin opening;

a collar connected to said second side of said flange and having an opening to discharge the drainage material containable within said collar;

a tubular member contained within said collar having a plurality of passages formed therein, each of said passages being separate from and positioned above said second side of said flange, each of said passages being formed substantially transverse to the longitudinal axis of said tubular member so that the drainage material flows through at least one of said passages into said tubular member;

an outlet member connected to said tubular member and held in said collar opening for carrying the drainage material from said collar; and a locking member contained within said collar and adapted for holding the drainage strip in the skin opening.

19. A drainage device for attachment to the skin of a patient while overlying an opening in the skin tissue and adapted for holding a drainage strip which is insertable into the opening to permit drainage thereof, said device comprising:

a flange including a first side for sealingly engaging the skin and a second side opposite said first side, said flange having an inlet therethrough to overlie the opening in the skin tissue to permit entry of drainage material from the skin opening;

a collar connected to said second side of said flange and having an opening to discharge the drainage material containable within said collar, said collar including a first wall and a second wall in which the vertical dimension of said first wall is greater than said second wall so that drainage material passes below said second wall, said collar having a channel formed between said first and second walls for carrying the drainage material received below said second wall; and a locking member connected to said collar and adapted for holding the drainage strip in the skin opening.

20. A drainage device for attachment to the skin of a patient while overlying an opening in the skin tissue and adapted for holding a drainage strip which is insertable into the opening to permit drainage thereof, said device comprising:

a flange including a first side for sealingly engaging the skin and a second side opposite said first side, said flange having an inlet therethrough to overlie the opening in the skin tissue to permit entry of drainage material from the skin opening;

a collar connected to said second side of said flange and having an opening to discharge the drainage material containable within said collar, said collar including a first wall and a second wall in which the vertical dimension of said first wall is greater than said second wall;

a plurality of spaced projecting members connected to an edge of said second wall and extending adjacent to said flange to define a plurality of passages between said projecting members to permit entry of the drainage material; and a locking member connected to said collar and adapted for holding the drainage strip in the skin opening.

21. A drainage device for attachment to the skin of a patient while overlying an opening in the skin tissue and adapted for holding a drainage strip which is insertable into the opening to permit drainage thereof, said device comprising:

a flange including a first side for sealingly engaging the skin and a second side opposite said first side, said flange having an inlet therethrough to overlie the opening in the skin tissue to permit entry of drainage material from the skin opening;

a collar connected to said second side of said flange and having an opening to discharge the drainage material containable within said collar, said collar having a first wall and a second wall in which said first wall has a greater circumferential dimension than said second wall, said collar including a channel generally perpendicular to said flange and formed between said first wall and said second wall for carrying the drainage material to said opening in said collar; and a locking member connected to said collar and adapted for holding the drainage strip in the skin opening.

22. The device, as claimed in claim 21, wherein: said collar is an annulus.

23. A drainage device for directly contacting a portion of the skin of a patient while overlying an opening in the skin tissue and adapted for holding a drainage strip to permit proper drainage of the skin opening, said device comprising:

a flange including a first side for sealingly engaging the skin of a patient and a second side opposite said first side, said flange having an aperture therethrough for exposing the opening in the skin tissue to receive the drainage therefrom;

collar means sealingly connected to said second side of said flange and including a first wall and a second wall with a channel formed therebetween;

a locking member connected to said collar means and adapted for holding the drainage strip in the skin opening, said locking member including a pair of resilient wings connected to said collar for receiving the drainage strip therebetween.

24. The device, as claimed in claim 23, wherein:

said locking member further includes a cross member connected to ends of said wings and held in said channel to support said wings within said collar means.

* * * * *